United States Patent [19]
Jeacock et al.

[11] Patent Number: 6,014,630
[45] Date of Patent: Jan. 11, 2000

[54] CUSTOMIZED SYSTEM FOR PROVIDING PROCEDURE-SPECIFIC PATIENT EDUCATION

[75] Inventors: Harvey F. Jeacock, West Redding; Elliott B. Nowak, Brookfield, both of Conn.

[73] Assignee: Patient Education Services, Inc., West Redding, Conn.

[21] Appl. No.: 08/112,191

[22] Filed: Aug. 26, 1993

[51] Int. Cl.[7] .................................................. G06F 17/60
[52] U.S. Cl. ............................................. 705/3; 705/2
[58] Field of Search .................... 364/413.01, 413.02, 364/401; 395/145, 146, 149, 600

[56] References Cited

U.S. PATENT DOCUMENTS

| | | | |
|---|---|---|---|
| 4,346,442 | 8/1982 | Musmanno | 364/408 |
| 5,056,029 | 10/1991 | Cannon | 364/468 |
| 5,065,315 | 11/1991 | Garcia | 364/413.02 |
| 5,148,366 | 9/1992 | Buchanan et al. | 364/419.14 |
| 5,225,976 | 7/1993 | Tawil | 364/401 |
| 5,267,155 | 11/1993 | Buchanan et al. | 364/419.14 |
| 5,277,188 | 1/1994 | Selker | 128/696 |

OTHER PUBLICATIONS

Fulda, PO, "PDQ: the National Cancer Institutes computerized database for physicians," Apr. 1990, pp. 49–50.
Rodewald et al, "Method for developing & maintaining a powerful but inexpensive computer database of clinical information about emergency dept. patients," 1992.

*Primary Examiner*—Stephen R. Tkacs
*Attorney, Agent, or Firm*—St. Onge Steward Johnston & Reens LLC

[57] ABSTRACT

A system for producing individualized patient educational reports for patients about to receive medical procedures, such as surgery, the reports including data relating to the particular medical procedure, the particular medical facility, and the particular physician. The system includes a medical procedure database storing data as to a plurality of medical procedures, a medical facility database storing data as to how the medical procedures are carried out at that particular medical facility, a physician database storing data as to how individual physicians vary the medical procedures, a method for manually entering individual patient data and for selecting the particular medical procedure, the particular medical facility, and the particular physician to be used for the individual patient, a formatting technique for taking the selected medical procedure, the selected medical facility, and the selected physician and preparing a report providing information for the patient as to the medical procedure the patient is about to undergo, and a printer for printing out the report. The report advises the patient what to anticipate and what is expected of him.

20 Claims, 10 Drawing Sheets

6,014,630

CUSTOMIZED SYSTEM FOR PROVIDING PROCEDURE-SPECIFIC PATIENT EDUCATION

FIELD OF THE INVENTION

This invention relates to the field of information collation services for patients. In particular, it relates to a method and system for creating a patient information document with procedure-specific information, to be given to a patient about to undergo a medical procedure, such as surgery, the information being customized to the requirements of the particular medical facility, the surgeon or physician, and the patient himself.

BACKGROUND OF THE INVENTION

Today, patients often enter into medical procedures without a full understanding of what is to take place, and of what is required of them. This can be difficult for them physically and psychologically, and can lead to medical problems and financial consequences.

Each patient is different, each surgeon has his own system for each procedure, desired medications, and desired post-procedure practices; and each medical facility has its own pre- and post-procedure patient requirements. It would be valuable for the patient if he could be apprised in advance of these as it affects his case. Our invention is directed to a system for quickly and accurately providing that information to the patient in written form. In addition, it permits modifications of that information by health care providers, as may be necessary, to adapt it to particular problems relative to the specific patient.

BRIEF SUMMARY OF THE INVENTION

We use a database system to retain the desired information as to various medical procedures, practices of individual physicians, and methods followed by various medical facilities, and a program to select desired ones of these for a particular patient and to modify it as a doctor may require for that patient.

In essence, the database includes various templates of information as they relate to providing the patient's required knowledge and understanding of (a) systems used by the specific facility for the particular procedure to be undergone; and (b) specific techniques used by the doctor performing that procedure. The latter include additional database templates relating to pre-procedure testing necessary and post-procedure follow up. These templates, which may be called "default templates," result from the user providing information to a database or computer relating to the patient, surgeon, procedure, facility, and the like (i.e., answering a series of questions put by a computer relating to these matters). They can then be accepted as is or be customized as necessary for any unique problems of the patient himself. They are then formatted and printed. In the event that the user does not customize the templates, the selected default templates are printed as is.

The result is a multi-page personalized patient document which can be given to the patient, telling him what he should do in preparation for the procedure, what he should expect at the hospital, what post-operative procedures to follow, and explaining details of recovery patterns.

The system has the advantage that use of the database and of a computer created check list assures that all necessary information will be provided, that any individual problems will be resolved in advance, and that the patient will have all necessary information in writing. Because of its completeness, it reduces the possibility of the doctor and/or the hospital being sued for malpractice because of lack of patient knowledge or instructions.

DESCRIPTION OF THE DRAWINGS

FIGS. 3a to 7d are flow charts showing the steps taken in the preparation of the report.

FIGS. 3a and 3b together are the flow chart showing overall procedures followed when using the system.

FIG. 4 is the subroutine for entering patient information.

FIG. 5 is the subroutine for selecting those pre-procedure tests which are required or should be made, and for setting a time and place for each of the tests.

FIG. 6 is the subroutine for selecting follow-up procedures.

FIG. 7d is the subroutine in which the physician can override the originally selected anesthetic.

DETAILED DESCRIPTION OF THE INVENTION

Introduction

Figure 1:
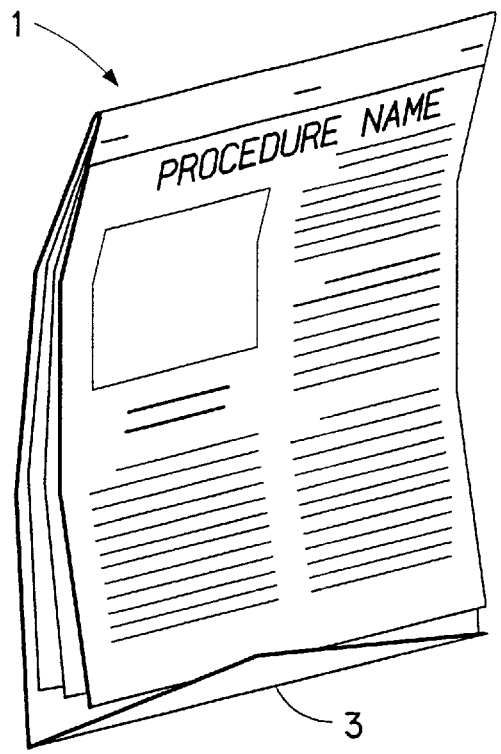
FIG. 1 is a perspective view of the final patient document, prepared by computer. This document is given to the patient.

This invention relates to the generation of a computer-generated patient information document (1, FIG. 1). The system can be used by hospitals, free-standing surgical facilities, HMOs, and surgical practices, etc. It will provide the patient in advance of surgery with (a) important pre-admission and pre-surgical requirements; (b) important post-surgical instructions including limits of activity and dietary restrictions; (c) self-care information with illustrations where appropriate; and (d) answers to the most frequently asked patient questions. This data comes primarily from computer databases carrying templates and document formats for procedure-specific patient information. These databases will have been prepared in advance with the assistance of board qualified surgeons and nursing personnel and include instructions specific to the individual facilities and physicians. They provide default data which can be modified in any specific situation to provide instructions specific to a particular patient.

The software associated with the system has been prepared such that:

(a) Each medical facility can tailor the pre-admission details and the day of surgery (or other procedure) patient instructions to their own requirements and can save these requirements in their database template. This information can then be used as needed and, since it can be modified for a specific situation, will vastly improve upon the type of information currently distributed in pre-printed booklets and the like.

(b) Each physician can set up physician-specific templates for each of the surgical procedures he practices. These will contain his variations on the patient instructions for the pre-procedure and post-procedure periods along with other information such as when the sutures will be removed, and the like. This will be saved in the physician's database under that doctor's identification number for use with patients about to undergo a particular procedure.

(c) Each multiple practice or hospital can have all of the physician specific variations for the procedure stored in the database under each physician's name or identification number, for use with patients that are to undergo that procedure.

All of this results from the user following routines presented by the computer while the document is being prepared. This system assures the user that the resulting patient information document is complete and covers all the desired subjects.

The Patient Document

The end result of the use of this system is the preparation of a detailed patient document or report 1 (with a self-mailer 3) which is given or mailed to the patient in advance of the procedure. This report will be in sufficient detail so that the patient is adequately educated as to the procedure to be followed, and knows what is expected of him and what he can expect. This makes for a better doctor-patient relationship and tends to put the patient more at ease.

A typical individualized patient document would include:

(a) The name of the procedure to be undertaken.

(b) The patient's and doctor's names, with necessary telephone numbers.

(c) Tests which must be performed in advance, giving times and locations.

(d) Questions on particular problems, such as allergies, and whether existing medications should be discontinued.

(e) What the patient should do and expect on the day of the procedure.

(f) Type of anesthesia to be used, its effects, and the length of the procedure.

(g) Information as to after effects, discomfort, healing time, and post-procedure medications.

(h) Limitations of activities and necessary therapy after the procedure.

(i) Dietary and nutrutional information.

(j) Problems which may arise, and what to do about them.

(k) Date and place of first post-procedure visit with the doctor.

Other or different subjects can be provided depending upon the desires of the user. Further, the subjects covered can be modified for each individual report to satisfy individual problems of a specific patient.

As can be seen, an individualized patient document such as this is valuable to the patient. It is also valuable to the doctor since he knows that all required information has been given to the patient, with nothing omitted, and the patient will have clear, understandable, written instructions to follow.

Comprehensive as these reports are, once the databases are set up, their preparation is simple and quick.

Preparation of the Patient Document

Flowcharts will be described below. However, these will be easier to understand if the system operation is first reviewed.

Figure 2:
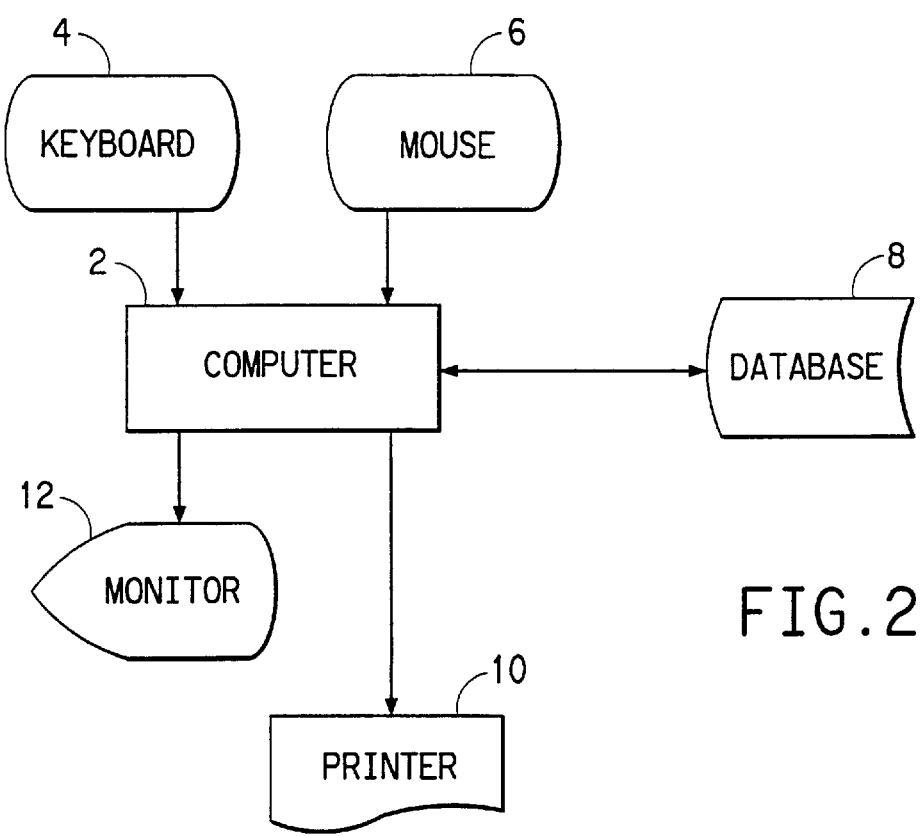
FIG. 2 is a generalized chart of the input-output system used.

System operation is shown in FIG. 2. A computer 2 with a keyboard 4 and a mouse 6 is used by the operator to enter the initial data requested and answer questions, as presented on the monitor 12. The types of data requested and the questions are carried in the computer's database 8; they will vary with the nature of the information keyed into the computer.

When a physician is selected and the procedure has been determined, the PC or workstation operator will first type in the patient's name, sex, and age so the computer can establish the category of patient. Next various questions appear on the computer monitor 12, sometimes with point and click answers. These determine the procedure, the hospital or other medical facility, and the physician's name. Required tests appear, and dates and places can be inserted. Dates and places for follow-up appointments must be answered. Since the questions to be answered have been pre-programmed, the user can be assured that when he has completed the task all the necessary matters have been covered.

The patient document 1 is then formatted in the computer and printed out by printer 10. If the information needs to be tailored to any individual requirements, this, of course, is done before printing.

Flowcharts

FIGS. 3*a* to 7*d* are flowcharts showing how the system is used to prepare an individual report.

Figure 3A:
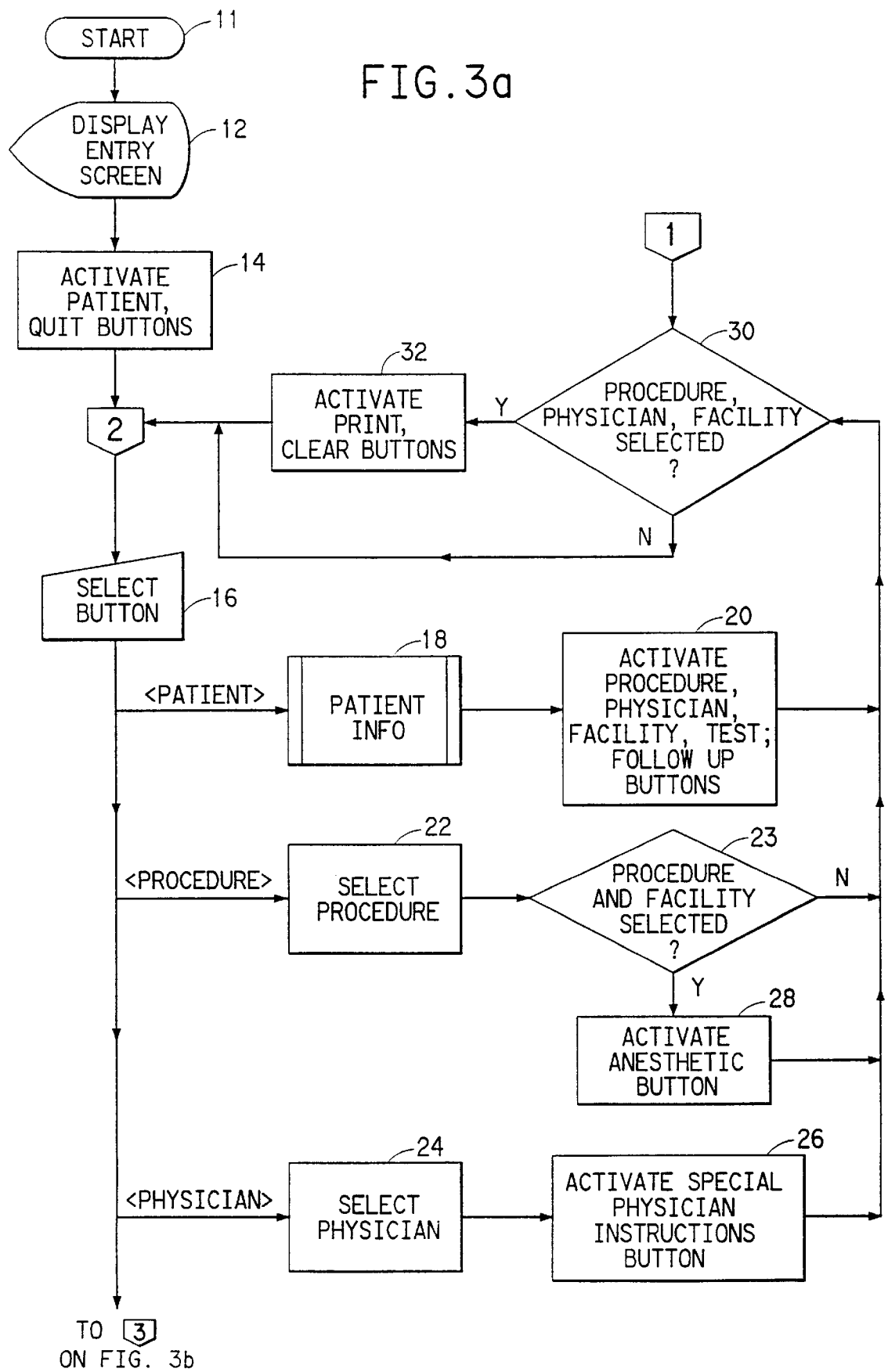
Figure 3B:
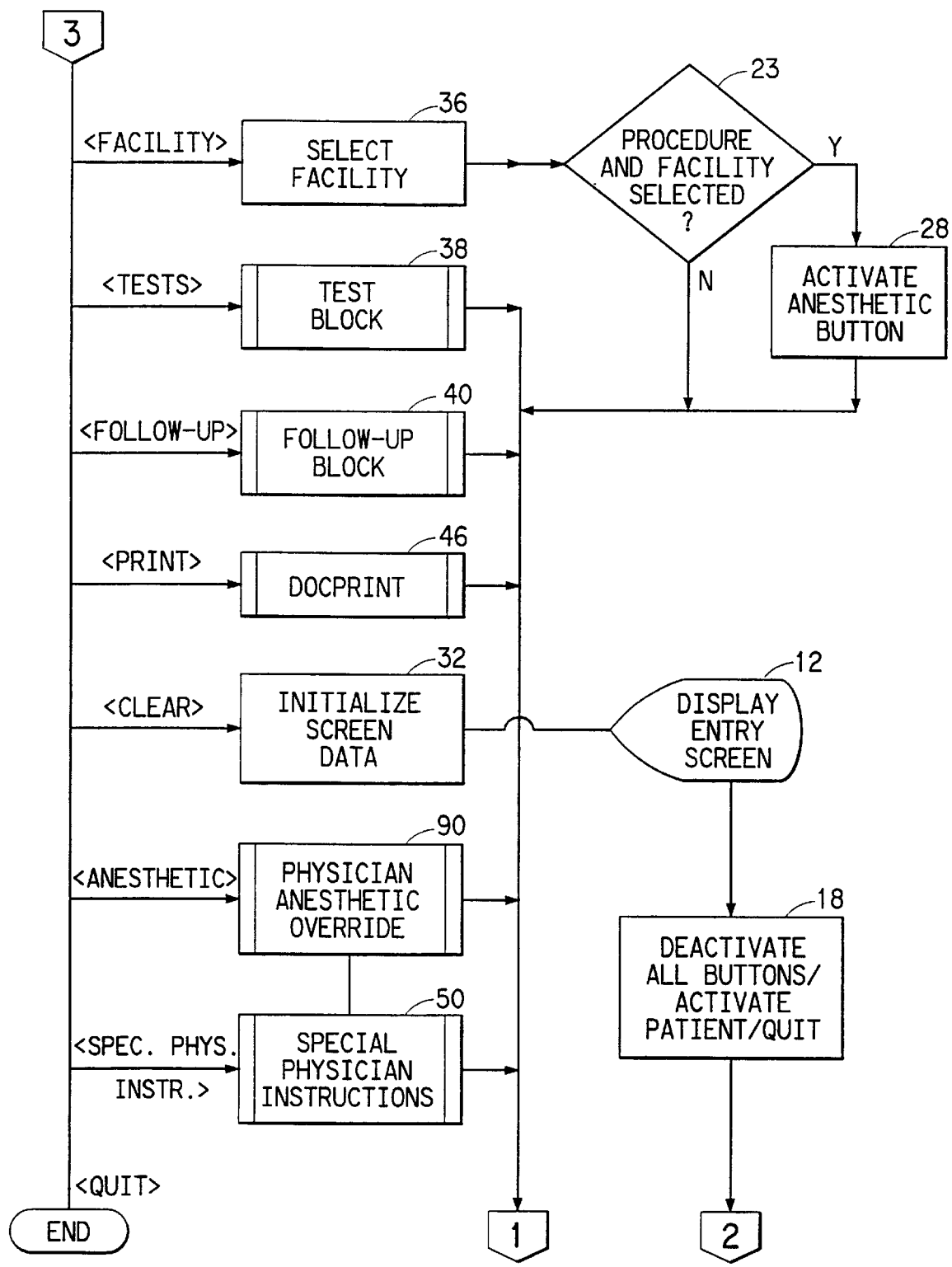
Figure 4:
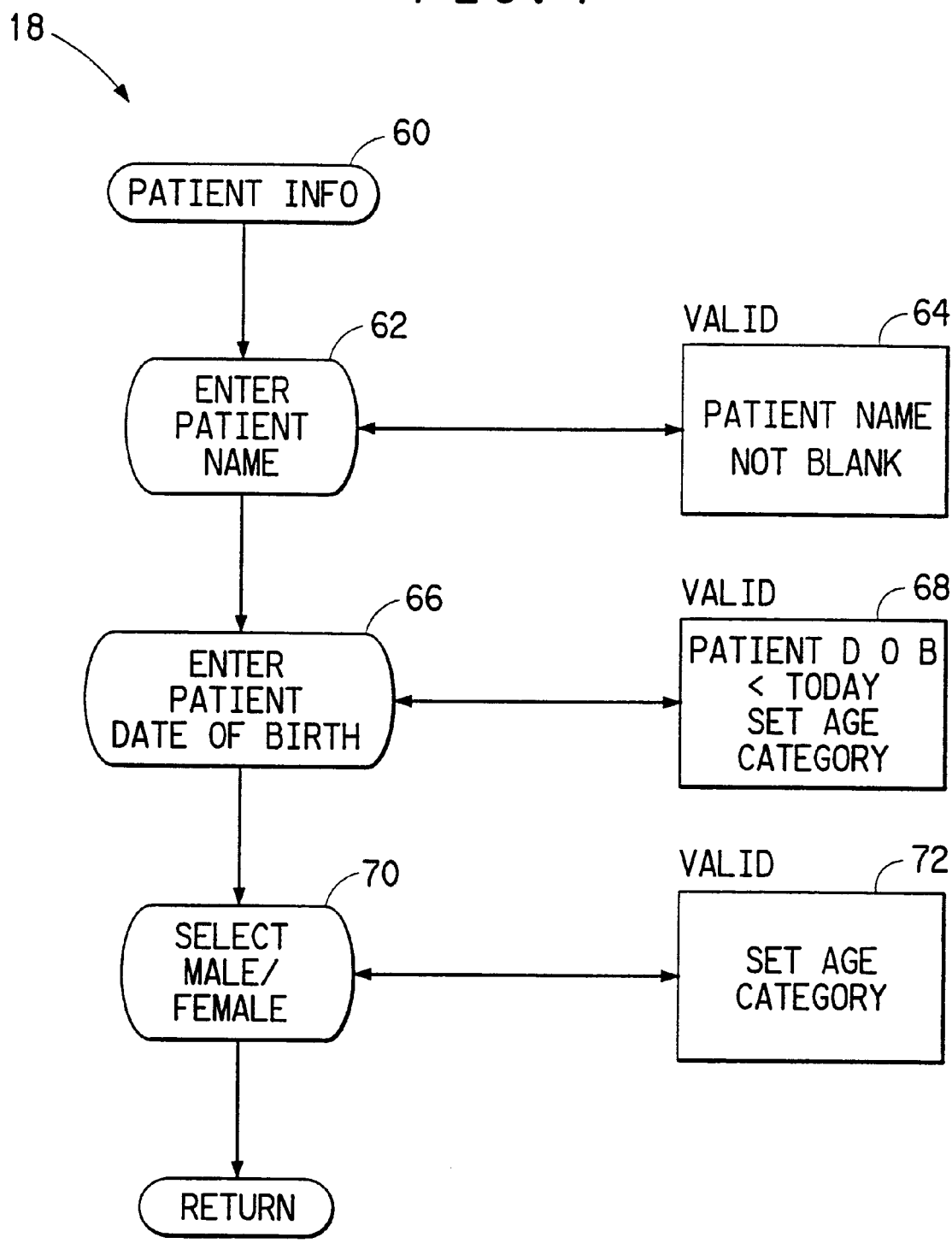

FIGS. 3*a* and 3*b* together set forth the overall method of using the system. The start 11 brings up the display entry screen 12 which presents an activate/quit button 14 and then a series of activate buttons and fields related to different entries. These normally should be pressed in a particular sequence and will not be functional if necessary preliminary information has not been entered.

The first button is the patient button 18 for identification of the patient and data with respect to the patient. This button performs the patient information subroutine 18 (FIG. 4) to receive patient data. After the patient information button 60 is selected, the patient's name 62 is keyed in, and the computer makes a validity check 64 to corroborate that. It then asks that the date of birth be keyed in 66, after which it sets the patient age category 68. The patient's sex is keyed in 70, and, again, the proper templates for that sex are determined 72. This provides for use of those pre-set database templates which have been designed for that age category.

Figure 5:
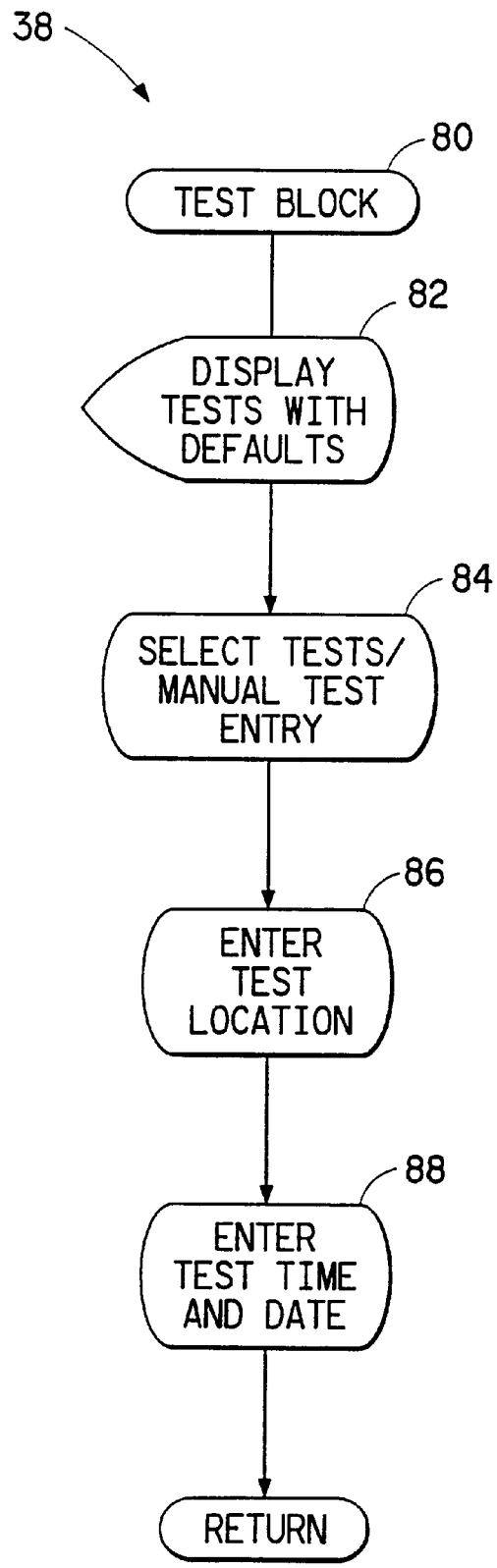
Figure 6:
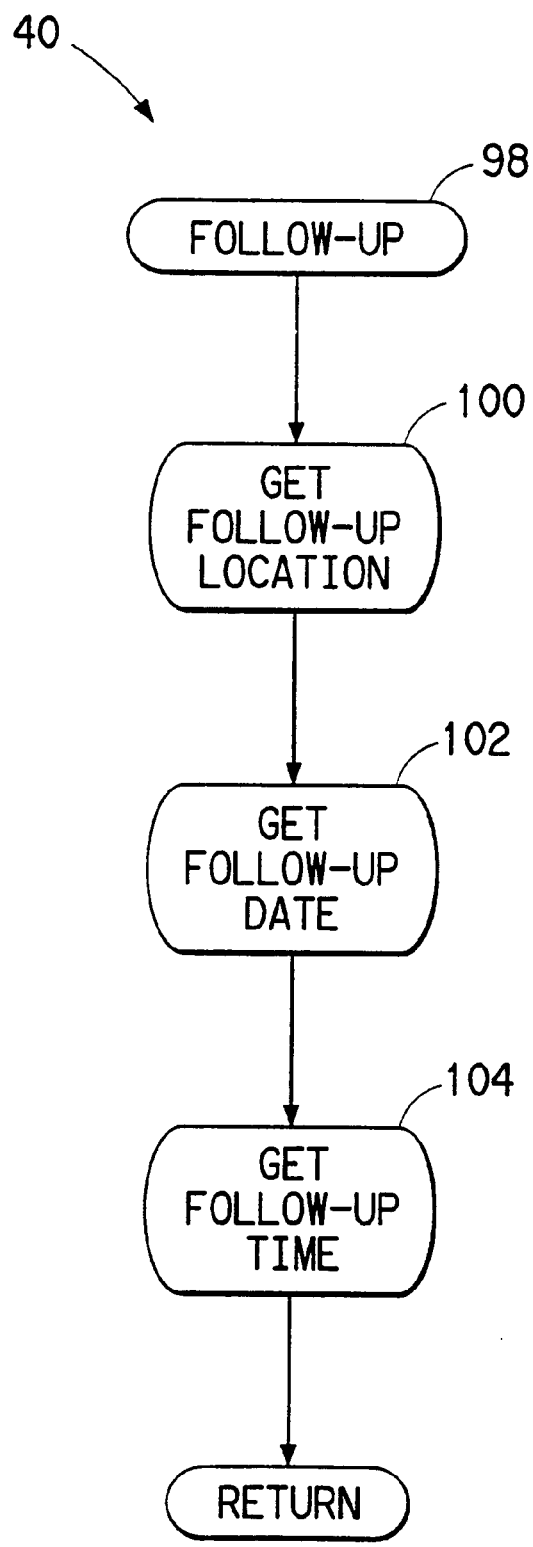

Completion of the patient data subroutine, by entry of the required information, will activate the "activate process" 20 which then allows use of subsequent entry systems, i.e., select procedure button 22, the select physician button 24, the select facility button 36, the test subroutine 38 (FIG. 5), the follow-up subroutine 40 (FIG. 6).

Actuation of any of these buttons brings up a screen requesting specified information. This information must be provided before proceeding. Once it is provided, the logic goes to the decision block 30, which determines whether or not the routines have been completed for selecting the procedure, the facility, and the physician. If "no" the operator is returned to the select button 16 for the entry of further information.

After entering the patient data, the operator then selects procedure 22, which then directs the computer to the database template for that procedure. The physician is then selected 24, which activates the physician's special instructions 26 for that procedure, and is used to modify the procedure template accordingly. This is followed by selecting the facility 36.

The test subroutine 38 is then called up by keying test button 80; and the subroutine of FIG. 5 is followed. Test button 80 is keyed, bringing up display 82 showing a list of pre-operation tests. This list has a default setting, pre-selecting desired tests. The operator then selects desired tests 84 and can add tests not shown on the screen. For all tests selected their location 86 and their time 88 can be entered. Additional tests can also be added. This subroutine is now complete and the logic returns to FIG. 3*b*.

If, due to particular conditions, the physician wishes to change the anesthetic from that preferred by the facility for the particular procedure, anesthetic override button 90 (FIG. 8) is pressed, and the anesthetic override screen appears, showing alternative choices. The desired anesthetic is selected from the anesthetic select list 94 which appears.

The last item to be entered is the follow-up procedure 40 (FIG. 6). After calling up this subroutine, the operator keys in the location 100, the date 102, and the time 104. The logic now returns to FIG. 3*b*.

The last entry is the subroutine 50 for special physician's instructions for this patient.

Figure 7A:
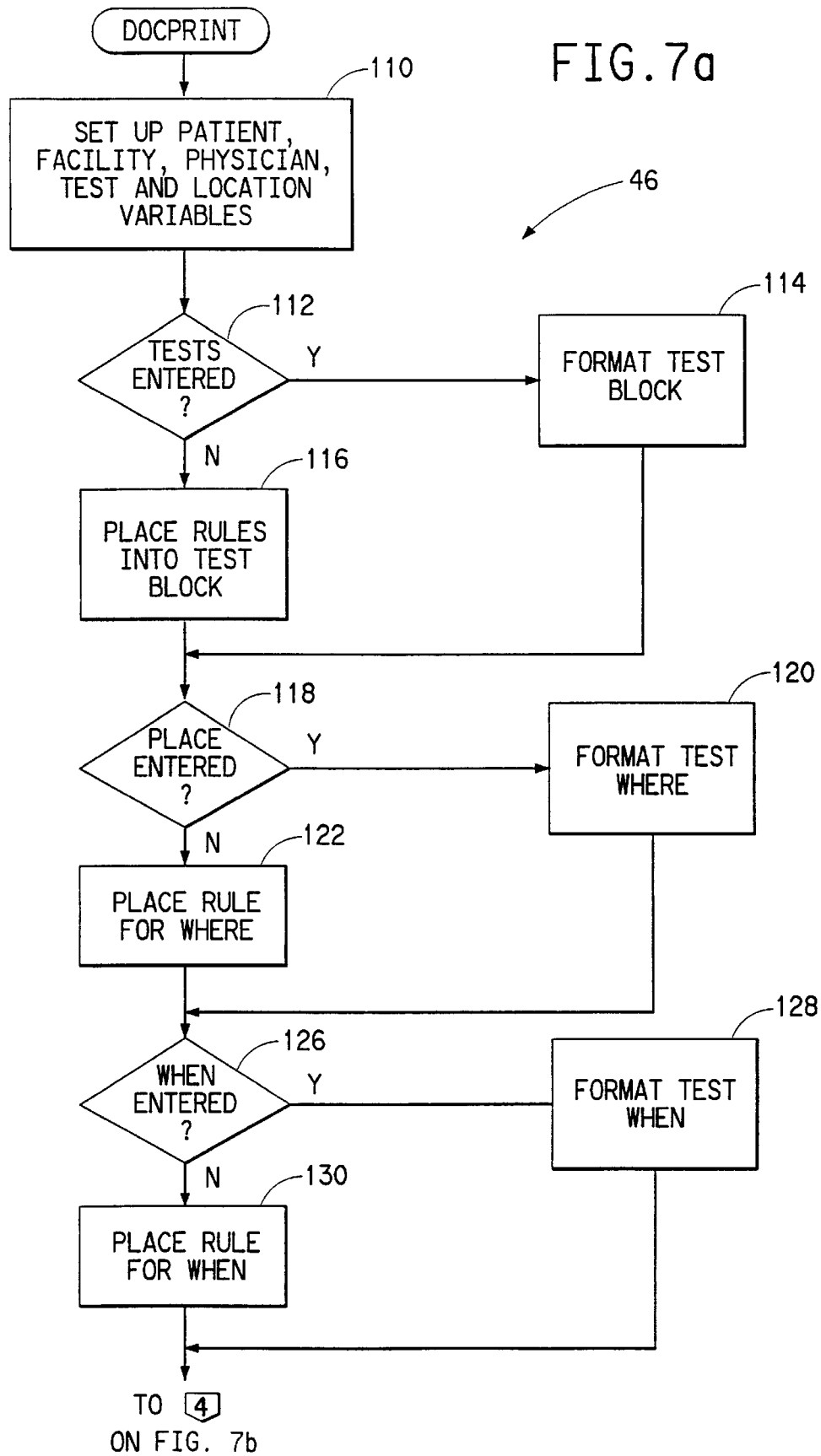
FIGS. 7a, 7b, and 7c are the subroutines for substituting for variables contained in the database templates and formatting the document.
Figure 7B:
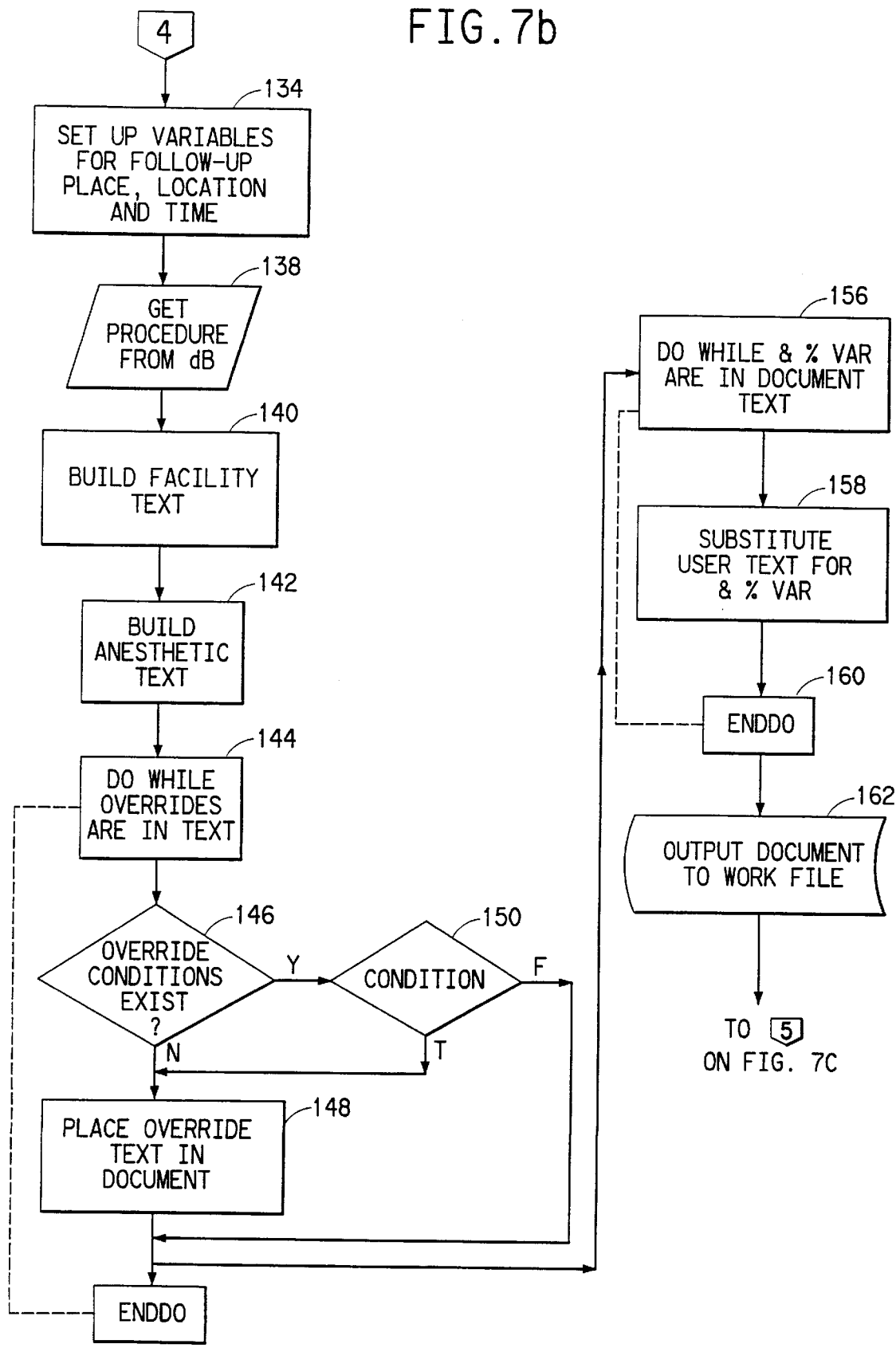
Figure 7C:
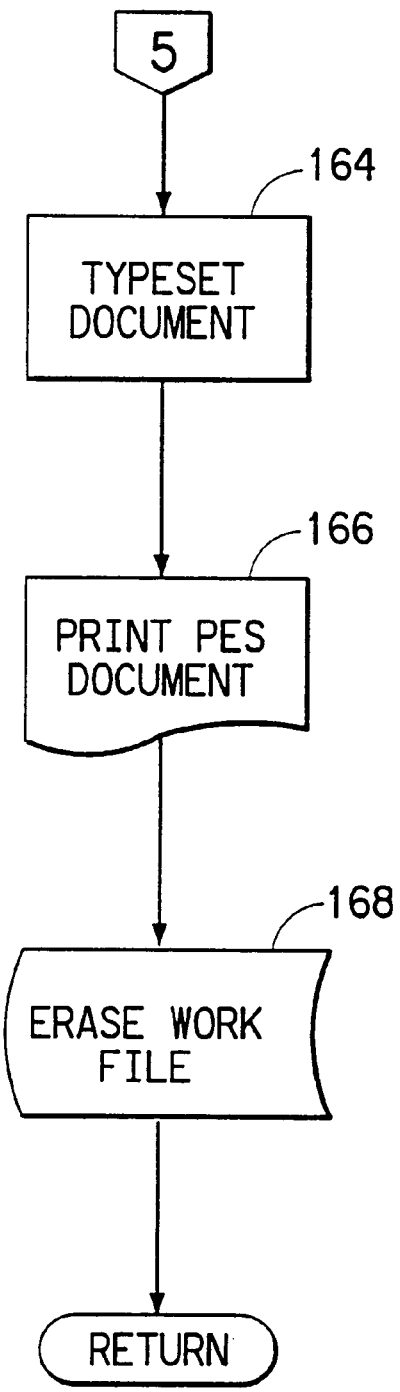
Figure 7D:
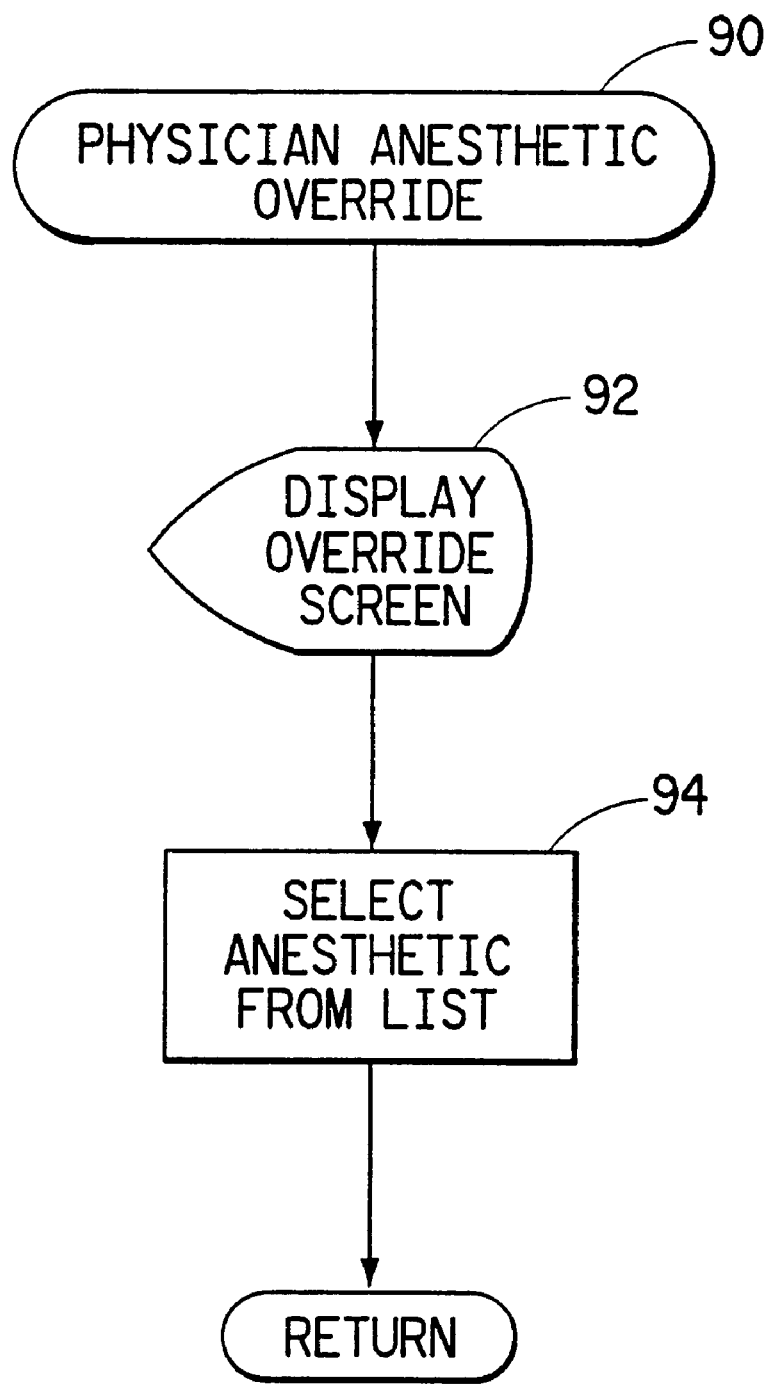

When these matters have been entered, the decision block 30 is a "yes", which activates the print and clear buttons 32. This allows the user to select the document print subroutine button 46 (FIGS. 7*a* to 7*c*). This subroutine, as will be described below, pulls up required information from the database as to the matters entered, and substitutes user information for the variables in the procedures. It then puts the data in form for printing.

The formatting subroutine 46 is found in FIGS. 7*a*, 7*b*, and 7*c*, and serves check completeness and to format the finished report for printing. It starts by formatting data 110 that has been entered on the patient, the doctor, the facility, and the tests. It checks to determine if the tests have been entered 112, and, if so, formats them for printing 114. If not, blank lines are put into the document 116. It then does the same for "place of tests" 118; if entered, it is formatted for printing 120; if not, blank lines are formatted 122. It then does the same for "when" 126; if entered, it is formatted for printing 128; if not, blank lines are formatted 130.

The same procedure is then followed for information as to follow up 134.

Data on the procedure to be undertaken is obtained from the database 138, for the facility 140, and for the anesthetic 142. A check is then made to determine if any aspect of these have been changed for this procedure 144, and, if so, these are checked to see if any override conditions exist 146 (this allows for selection of text on certain conditions). If not, the overrides are placed in the document text 148. If so, they are checked to determine if proper in the present situation 150; if proper, they are used; if not, they are eliminated. It reviews the document until all override conditions have been substituted for.

The variables (age, doctor, phone numbers, etc.) are then called up 156 and entered in the text by substitution for the original information on the templates 158. This is checked for completeness 160, and the completed document stored. The finished report (patient education service document) can then be formatted 164 and printed 166. If desired, it can thereafter be erased from memory 168.

As can be seen, our system uses a default technique for choosing templates. That is, standard templates are used, depending upon the facility, the surgeon, the procedure, and the patient. These default templates can, however, be modified for specific conditions.

It should be realized that the templates used contain more than bare-bones information. They also contain considerable "boilerplate," such as introductory paragraphs explaining the purpose of the documents, and explanatory material regarding each of the steps, advising where to call if any problems occurs before the procedure, or afterwards, and the like. The result is that the report which the patient receives provides him with considerable useful information, and serves to put him at ease.

It should be understood that this system can be used for many procedures in addition to surgical procedures. These could include procedures such as, for instance, delivery of a baby, particular types of physical examinations, and dental procedures.

Software

As can be seen, this system is built up of a series of prepackaged templates or databases carrying information as to various procedures, facilities, physicians, pre-operative tests for specific procedures, and follow up practices for those procedures. Selected ones of these templates are used for a given patient situation and are varied as the individual case may require.

The templates also include formats providing the necessary descriptive language to put the final report into pleasant, readable, and "user-friendly" form.

Preparation of reports in a system such as the present one, therefore, requires use of a programmable database, programmed to carry out the functions set forth in the flowcharts included and described here. One such database, which has been successfully used by us, is called FoxPro made by Microsoft. Others can, of course, be used.

For formatting and typesetting, we use a publishing engine called dB Publisher Pro, made by Digital Composition Systems. This is programmed to produce the final desired layout of the report, including fonts, font sizes, graphics, document format, and pagination.

We claim:

1. A system for producing individualized patient educational documents for patients about to undergo medical procedures, such as surgery, said documents including data relating to said medical procedure to be undergone, the medical facility to be used, and the responsible physician, said system including a computer having a medical procedure database, a medical facility database, and a physician database, said medical procedure database storing data about a plurality of medical procedures, said medical facility database storing data about how said medical procedures are carried out at at least one medical facility, said physician database storing data about how individual physicians vary said medical procedures, manual entry means associated with said computer for entering data about a prospective patient and for selecting from said databases said medical facility, said medical procedure and said physician to be used for said patient, software in said computer for taking from said databases data about said medical procedure to be undergone, said medical facility to be used, and said responsible physician, and organizing a document providing information for said patient about the said medical procedure said patient is about to undergo, and a printer associated with said computer for printing said document, whereby said patient is advised in writing as to what to anticipate and what is expected of him.

2. A system as set forth in claim 1 including means for adding instructions to said document, prior to printing said document, said instructions varying information for said patient in the data being printed.

3. A system as set forth in claim 1 in which one of said databases includes pre-procedure and post-procedure instructions, and said system includes means for incorporating said instructions in said document.

4. A system as set forth in claim 3 in which said pre-procedure instructions includes specifications for pre-procedure tests.

5. A system as set forth in claim 1 including causing that data from said medical procedure database, said medical facility database, and said physician database to be included in said document.

6. A system as set forth in claim 1 in which said medical facility database stores data about how said medical procedures are carried out at a plurality of medical facilities.

7. A system as set forth in claim 1 in which said data about a prospective patient includes said patient's age and sex, and said medical procedures stored in said medical database vary depending upon age and/or sex.

8. A system as set forth in claim 1 in which one of said databases includes data about pre-procedure tests, and in which said manual entry means is usable to select particular ones of said tests, causing said computer to incorporate said selected test in said document.

9. A system as set forth in claim 8 including means for incorporating in said document times and places of said selected tests.

10. A system as set forth in claim 1 including a default means in said computer which, in the event no specific instructions are given in a particular instance to change the data about said medical procedure or about said physician's instructions, causes the document to contain said medical procedure and said physician's instructions.

11. A system for producing individualized patient educational documents for patients about to undergo medical procedures, such as surgery, said documents including data relating to said medical procedure to be undergone, the medical facility to be used, and the responsible physician, said system including
- a computer having one or more of the following databases: a medical procedure database, a medical facility database, and a physician database,
- said medical procedure database storing data about a plurality of medical procedures,
- said medical facility database storing data about how said medical procedures are carried out in at least one medical facility,
- said physician database storing data about how individual physicians vary said medical procedures,
- manual entry means associated with said computer for selecting at least one of said databases,
- software in said computer for taking selected data from said selected databases and organizing a document providing information for a patient about said medical procedure said patient is about to undergo and about said medical facility, said software including a default procedure requiring that said document include at least data on said medical facility and on said medical procedure, and
- a printer associated with said computer for printing said document,
- whereby said patient is advised in writing as to what to anticipate and what is expected of him.

12. A system as set forth in claim 11 including means causing all necessary data from said databases to be included in said document.

13. A system as set forth in claim 11 including means for adding specialized instructions to said document, prior to printing said document.

14. A system as set forth in claim 11 in which said computer includes a test database storing data about pre-procedure tests, whereby said manual entry means can be used to select tests from said pre-procedures and incorporate said pre-procedures in said document.

15. Apparatus for preparing patient documents which provide a particular patient with an individualized patient information document relating to a prospective medical procedure, including
- a computer having a database including templates of data on a plurality of medical procedures and templates of data on variations made to said medical procedures by particular doctors,
- a monitor associated with said computer, said computer being programmed to determine whether or not (1) that the user has specified said patient, (2) that the user has specified said medical procedure to be performed and the physician in charge of performing said medical procedure, and (3) that the user has specified any modifications in said templates of data for said prospective medical procedure as varied by said particular physician,
- software in said computer for formatting a patient document incorporating said templates,
- a printer associated with said computer for printing said patient document as so formatted
- means for changing said patient document before printing to make changes specific to said patient, and
- said computer programmed with a default setting which, if no changes are made to said patient document, causes said patient document to be formatted without modification of said templates for said medical procedure and said physician.

16. Apparatus for preparing patient documents which provide a particular patient with an individualized patient information document relating to a prospective medical procedure, including
- a computer having a database including templates of data on a plurality of medical procedures and templates of data on variations made to said medical procedures by particular doctors,
- a monitor associated with said computer, said computer being programmed to determine whether or not (1) that the user has specified said patient, (2) that the user has specified said medical procedure to be performed and the physician in charge of performing said medical procedure, and (3) that the user has specified any modifications in said templates of data for said prospective medical procedure as varied by said particular physician,
- software in said computer for formatting a patient document incorporating said templates,
- a printer associated with said computer for printing said patient document as so formatted, and
- said computer programmed not to print the patient document if the user has failed to indicate whether or not modifications to said templates should be made.

17. Apparatus for preparing patient documents which provide a particular patient with an individualized patient information document relating to a prospective medical procedure, including
- a computer having a database including templates of data on a plurality of medical procedures and templates of data on variations made to said medical procedures by particular doctors,
- a monitor associated with said computer, said computer being programmed to determine whether or not (1) that the user has specified said patient, (2) that the user has specified said medical procedure to be performed and the physician in charge of performing said medical procedures, and (3) that the user has specified any modifications in said templates of data for said prospective medical procedure as varied by said particular physician, software in said computer for formatting a patient document incorporating said templates, a printer associates with said computer for printing said patient document as so formatted, and said database including templates storing procedures used in differing medical facilities, said computer is programmed to require the use to identify the medical facility to be used, and the said template for said medical facility is included in the formatting of said patient document.

18. Apparatus for preparing patient documents which provide a particular patient with an individualized patient information document relating to a prospective medical procedure, including a computer having a database including templates of data on a plurality of medical procedures and templates of data on variations made to said medical procedures by particular doctors, a monitor associated with said computer, said computer being programmed to determine whether or not (1) that the user has specified said patient, (2) that the user has specified said medical procedure to be performed and the physician in charge of performing said medical procedure, and (3) that the user has specified any modification in said templates of data for said prospective medical procedure as varied by said particular physician, software in said computer for formatting a patient document incorporating said templates, a printer associated with said computer for printing said patient document as so formatted, and said computer is programmed to require identification of said patient's age and sex, and said templates of medical procedures include said templates which incorporate said medical procedures which differ depending upon said age and/or sex.

19. A method of preparing a patient document which provides a particular patient with an individualized document relating to the patient's prospective medical procedure, including the steps of storing information in a computer describing various medical procedures, the requirements of the medical facility to be used for said medical procedures, and the responsible doctor's variations of said medical procedures, programming the computer (a) to receive information from the user about the patient to be treated, said medical procedures, (b) to select stored information about said medical procedures, said requirements of the medical facility, said responsible doctor's variations of said medical procedures, and said responsible doctor to perform said medical procedures, and (c) to format a related document incorporating said procedures to conform to said responsible doctor's said variations and to conform to said requirements of said medical facility, and (d) to print said document, and thereafter keying into said computer patient data, identification of the medical procedure to be performed and of the doctor in charge, and printing Out said document.

20. The method of claim 19 in which said information as to said patient includes said patient's age and sex, said stored data about medical procedures includes data as to variations in said medical procedures with said age and sex of said patient, and said computer is programmed to select said medical procedure for said patient's age and sex, and including the step of keying in said patient's age and sex.

* * * * *